(12) United States Patent
Carver

(10) Patent No.: US 10,675,393 B1
(45) Date of Patent: Jun. 9, 2020

(54) AIRWAY ASSIST DEVICE

(71) Applicant: Alan R Carver, Odessa, FL (US)

(72) Inventor: Alan R Carver, Odessa, FL (US)

(73) Assignee: Dechoker LLC, Erie, CO (US)

( * ) Notice: Subject to any disclaimer, the term of this patent is extended or adjusted under 35 U.S.C. 154(b) by 0 days.

(21) Appl. No.: 15/210,944

(22) Filed: Jul. 15, 2016

Related U.S. Application Data

(63) Continuation-in-part of application No. 14/794,285, filed on Jul. 8, 2015, now abandoned, which is a continuation-in-part of application No. 13/830,574, filed on Mar. 14, 2013, now abandoned, which is a continuation-in-part of application No. 13/135,783, filed on Jul. 15, 2011, now abandoned, which is a continuation-in-part of application No. 12/928,690, filed on Dec. 15, 2010, now abandoned, which is a continuation-in-part of application No. 12/653,645, filed on Dec. 17, 2009, now abandoned.

(51) Int. Cl.
*A61M 1/00* (2006.01)
*A61B 17/24* (2006.01)
*A62B 18/02* (2006.01)
*A61M 39/24* (2006.01)

(52) U.S. Cl.
CPC ............ *A61M 1/009* (2014.02); *A61B 17/24* (2013.01); *A61M 1/0009* (2013.01); *A62B 18/02* (2013.01); *A61M 2039/2406* (2013.01)

(58) Field of Classification Search
CPC . A61M 1/0011; A61M 1/0009; A61M 1/0023
See application file for complete search history.

(56) References Cited

U.S. PATENT DOCUMENTS

| | | | |
|---|---|---|---|
| 3,939,830 A * | 2/1976 | da Costa | A61B 17/50 128/205.18 |
| 4,971,053 A * | 11/1990 | Tarrats | A61M 1/0009 128/205.19 |
| 5,338,166 A * | 8/1994 | Schultz | B65B 31/047 137/625.41 |
| 2005/0085799 A1* | 4/2005 | Luria | A61B 5/6803 606/1 |
| 2009/0175747 A1* | 7/2009 | LeBoeuf | F04B 33/00 417/545 |
| 2012/0221010 A1* | 8/2012 | DeLuca | A61B 17/24 606/106 |

* cited by examiner

Primary Examiner — Sarah A Simpson
(74) Attorney, Agent, or Firm — Craig R. Miles; CR Miles P.C.

(57) ABSTRACT

A device that helps clear a fluid or other material lodged in a person's throat has a barrel with an open proximal end and an opening laden distal end. A plunger is slidably disposed within the barrel such that the plunger, by being manually drawn outwardly, creates suction within the barrel drawing air through the opening. A single or multi-section tube, flexible on at least its distal end, is fluid flow connected to the opening and has a face mask along its length. The distal end of the tube is intubated with a person proximate the fluid or other material so that as the plunger is drawn outwardly through the barrel, the suction created within the barrel causes air to be drawing in through the tube and into the barrel thereby helping draw out and dislodge the fluid or other material. A backflow valve located on the barrel helps clear the barrel of such things as vomit that might have been drawn into the barrel.

23 Claims, 6 Drawing Sheets

AIRWAY ASSIST DEVICE

CROSS-REFERENCE TO RELATED APPLICATIONS

This application is a Continuation-in-Part of U.S. patent application Ser. No. 14/794,285 filed on Jul. 8, 2015, which is a Continuation-in-Part of U.S. patent application Ser. No. 13/830,574, filed on Mar. 14, 2013, which is a Continuation-in-Part of U.S. patent application Ser. No. 13/135,783, filed on Jul. 15, 2011, now abandoned, which is a Continuation-in-Part of U.S. patent application Ser. No. 12/928,690, filed on Dec. 15, 2010, now abandoned, which is a Continuation-in-Part of U.S. patent application Ser. No. 12/653,645, filed on Dec. 17, 2009, now abandoned, each application being incorporated herein by reference in its entirety.

BACKGROUND OF THE INVENTION

1. Field of the Invention

The present invention relates to a device that is inserted into a person's mouth and helps assist in opening the person's airway due to saliva or debris present within the person's throat via suction created by the device.

2. Background of the Prior Art

Parents of children, especially young children, tend to have many worries on their minds with regard to their children. From SIDS, to swine flu, to injuries due to falls, to the various ailments that can afflict children, parents' worries can sometimes seem daunting. One major fear for parents of young children is choking. Many young kids, typically those under the age of three, will put most everything and anything into their mouth. While some such items may simply be disgusting, other items, can get lodged in a child's throat leading to an airway closure, either partial or full, so that the child is unable to breathe, possibly leading to death. Manufacturers of toys and other items designed for small children put warning labels onto their products that alert parents to the presence of small parts that can pose a choking hazard. However, it is nearly impossible to keep every small item that is capable of choking a child out of the child's reach. Older children may have toys that have small parts which toys the younger child can easily gain access to, especially if the older child does not clean up after playing—children tend to lack the safety diligence of parents. While playing outside, a small child can easily place a rock or other object into his or her mouthing leading to choking. Even the most vigilant parent cannot maintain constant visual contact with the young child. It only takes a few seconds for a potentially disastrous situation to commence.

While emergency personnel are trained to reopen a child's breathing passage, brain damage begins after the brain has been deprived of oxygen for about three minutes, faster for younger children. Therefore, unless trained emergency personal are onsite almost immediately after the object lodges in a child's throat, the potential for an adverse outcome is great.

Although the potential for choking tends to be highest among young children, adults are not immune from the choking potential. Food going down the throat the wrong way can potentially lead to choking in an adult. If the adult is in a restaurant or other public place, another person can initiate the Heimlich maneuver on the choking person. Even if the person is not properly trained in the Heimlich, a less than perfect attempt can dislodge the closure causing material, even if it does cause minor injury to the choking person. After all, a cracked rib is far superior to death. However, in a relatively secluded place, such as a person's home where the person may be at home alone or only with his or her spouse, improperly lodged food has greater potential for choking. A person alone cannot perform the Heimlich on himself or herself. If a spouse is present and is either too feeble or too scared to perform the Heimlich, the next best resort is summoning emergency personal. As noted above, such summoning may not prove adequate.

What is needed is a device that can quickly assist in opening a person's airway caused by saliva, vomit or other material within the person's throat in order to prevent choking. Such a device must be very easy to use so that a person who has not used the device before and who may be in a panic, can quickly employ the device in order to remove the fluid or airway passage closing other material and potentially save a life. Ideally, such a device will be of relatively simple design and construction so as to be affordable to a large portion of the population.

SUMMARY OF THE INVENTION

The airway assist device of the present invention addresses the aforementioned needs in the art by providing a device that can be quickly deployed in the case of a throat fluid or other material and can remove the fluid or other material in order to help clear the person's airway. The airway assist device is designed to be very easy to use so that a person who is unfamiliar with the device can still employ the device effectively in a very rapid amount of time. A choking person can use the device on himself or herself. The airway assist device is of relatively simple design and construction so as to be relatively inexpensive to produce using standard manufacturing techniques so that it is relatively affordable to a large segment of the population.

The airway assist device is comprised of a barrel that has an open first proximal end, a first distal end that has an opening, and a hollow interior. The first distal end has an inner surface within the interior chamber. A plunger has a second proximal end and a second distal end. A plunger cap has a closed base and is affixed to the second distal end of the plunger. The plunger is slidably disposed within the barrel its second proximal end protrudes through the first proximal end of the barrel. When the plunger is inserted into the barrel and drawn outwardly through the first proximal end, suction is created within the hollow interior of the barrel and pressure equalizing air is drawn into barrel through the opening on the first distal end. When the plunger assembly is inserted into the barrel to a maximum extent (fully depressed), the plunger cap on the plunger abuts the inner surface of the first distal end of the barrel. A handle is attached to the second proximal end of the plunger and is used for manual slide control of the plunger within the barrel. A face mask has a cuff encircled dome and is connected to the barrel. A resilient tube has a first tube end attached to the opening at the first distal end of the barrel and a second tube end with the tube passing through the dome of the face mask making the second tube end of the tube is fluid flow connected with the hollow chamber of the barrel. This tube can be formed of more than one discreet section. As the plunger is drawn outwardly from the barrel, the outward draw creates suction within the interior chamber of the barrel drawing air into the barrel through the opening on the first distal end of the barrel, the air so drawn being routed into barrel via the tube which draws the air through its second tube end as a result of the suction created. An O-ring encircles the plunger cap. A relief ring encircles the plunger cap and is positioned concentric with the O-ring. The relief ring has at least one longitudinal slit on an outer surface thereof, the slit allowing air to pass therethrough and in order to regulate a pressure of the suction within the barrel. A positive pressure backflow valve is located on the first distal end of the barrel. A receptacle is fluid flow connected to the backflow valve. A sound producing device is attached to the barrel or to the plunger or to the face mask for producing an instructional audio message on use of the suction device. A retainer cap is attached to the first proximal end of the barrel and prevents withdrawal of the plunger assembly from the barrel.

BRIEF DESCRIPTION OF THE DRAWINGS

Similar reference numerals refer to similar parts throughout the several views of the drawings.

DESCRIPTION OF THE PREFERRED EMBODIMENT

Figure 1:
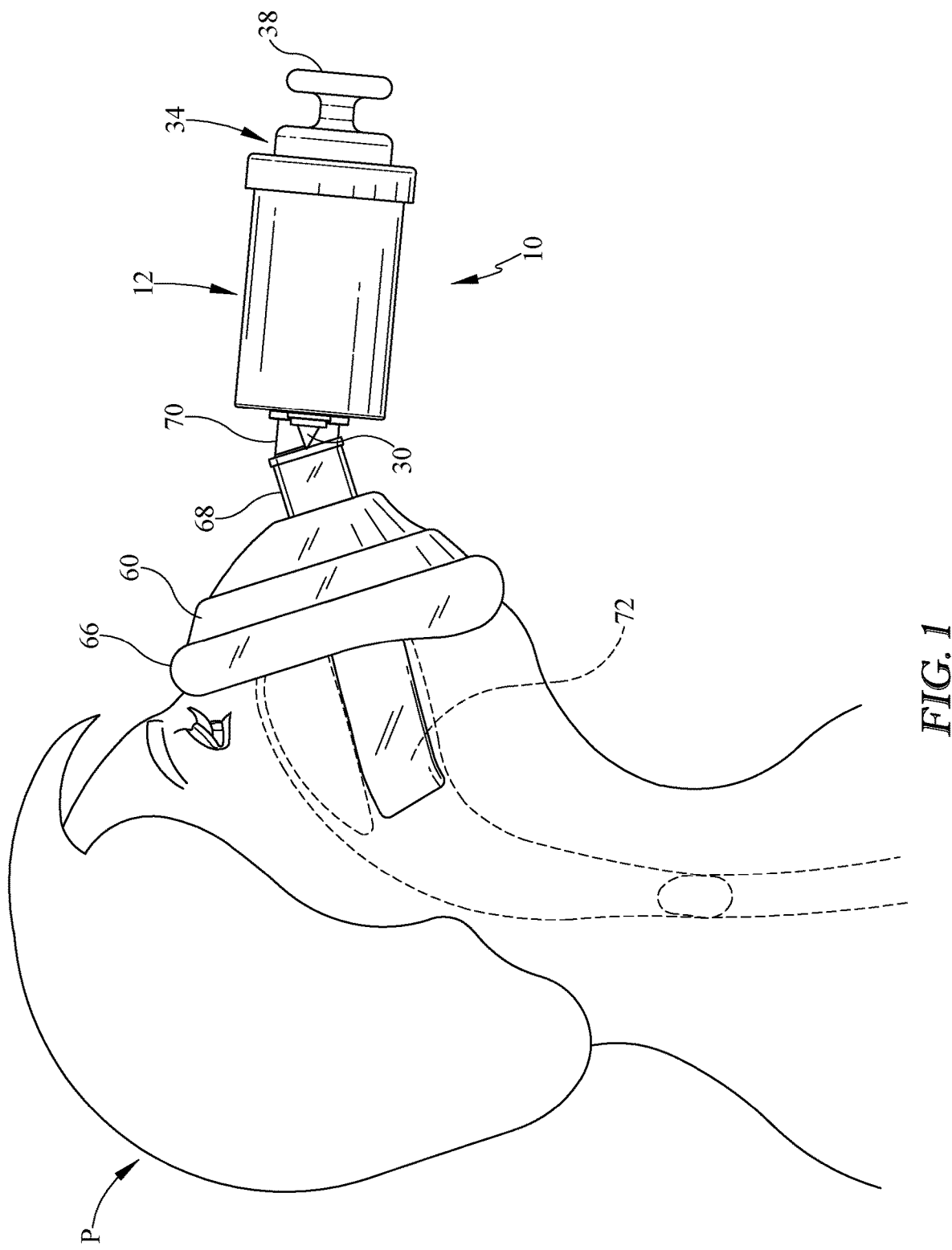
FIG. 1 is an environmental view of the airway assist device of the present invention being used on a person with a fluid or other material in the throat.
Figure 2:
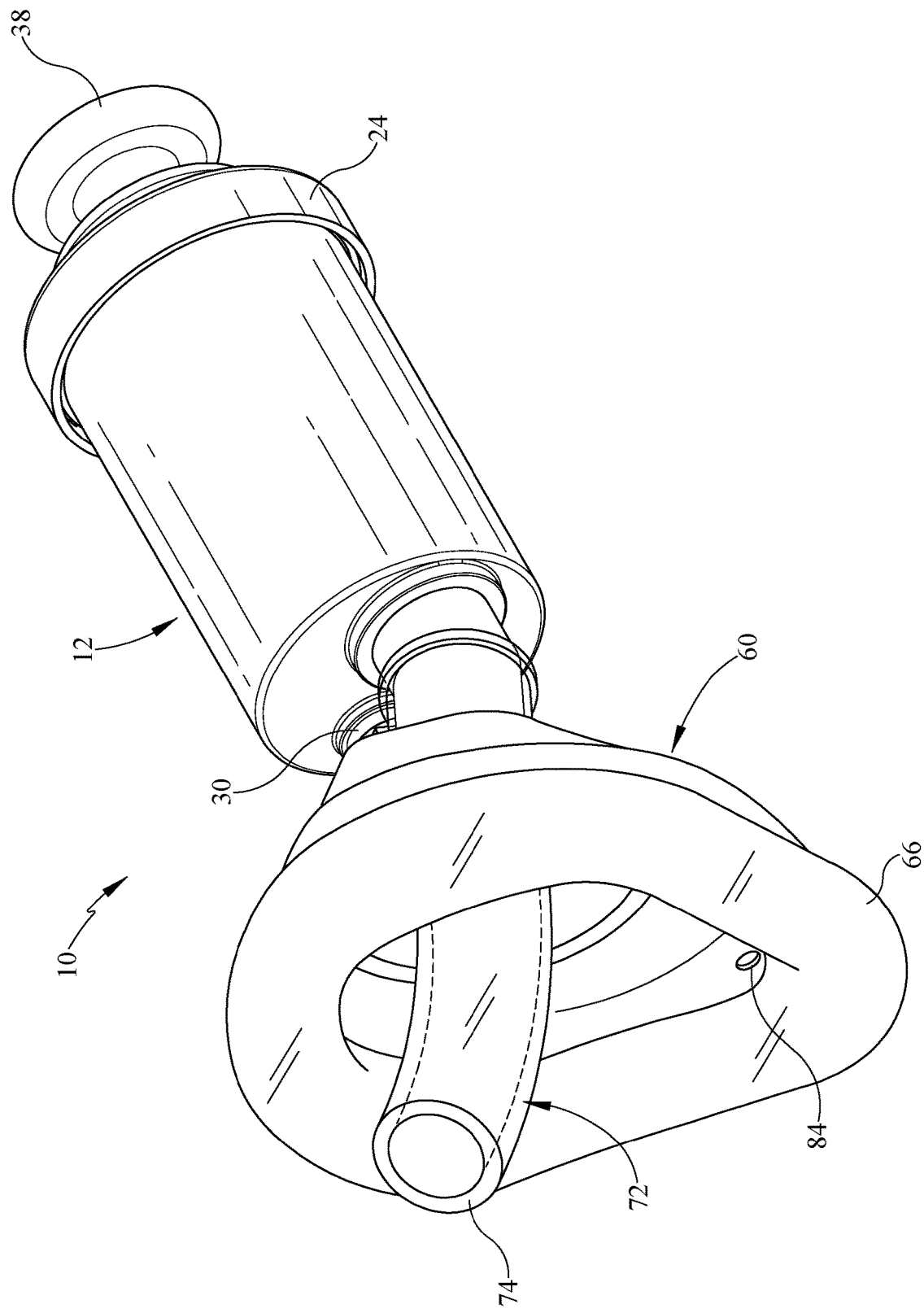
FIG. 2 is a perspective view of the airway assist device.
Figure 3:
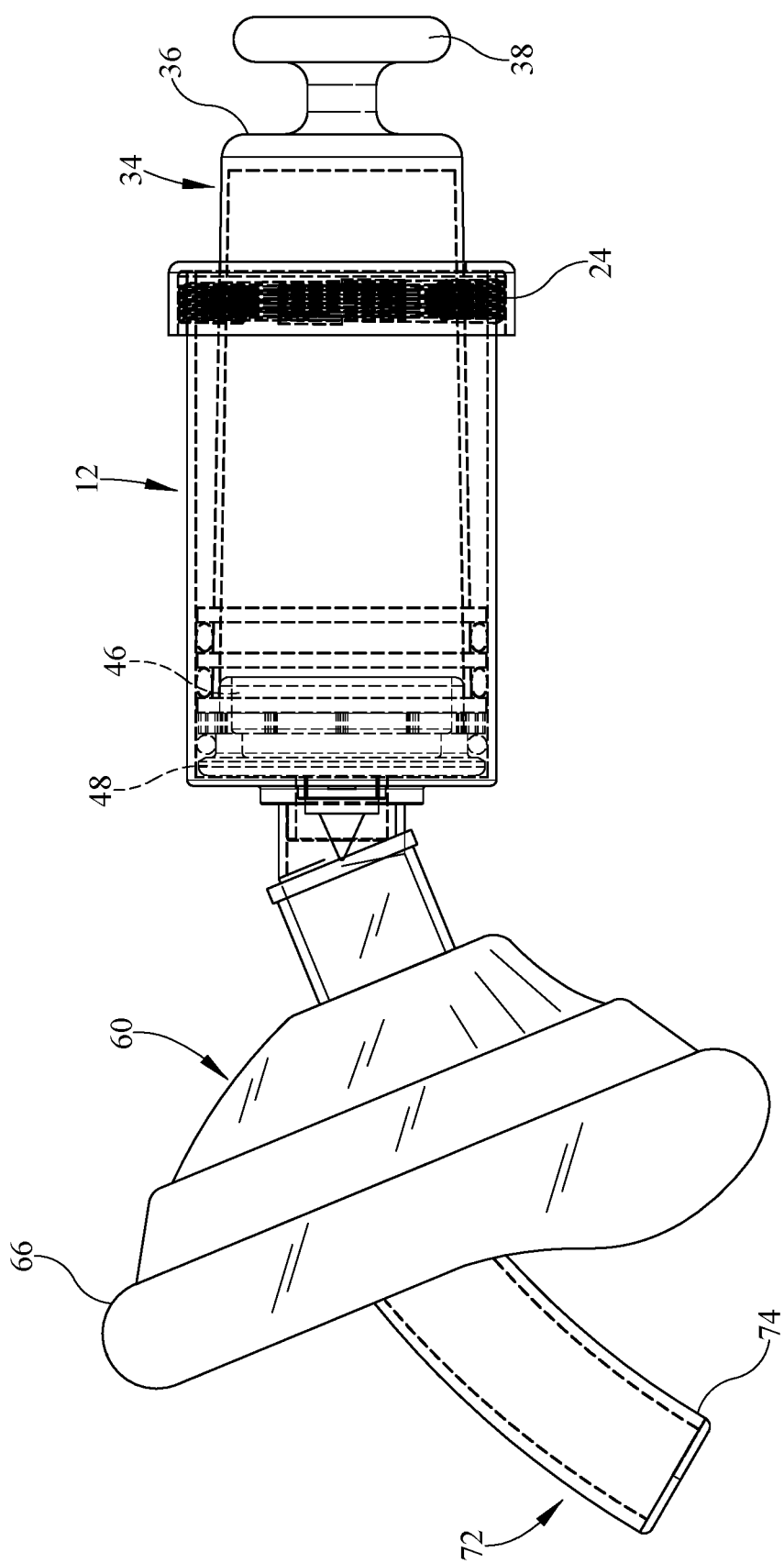
FIG. 3 is a side elevation view of the airway assist device with the plunger assembly fully depressed.
Figure 4:
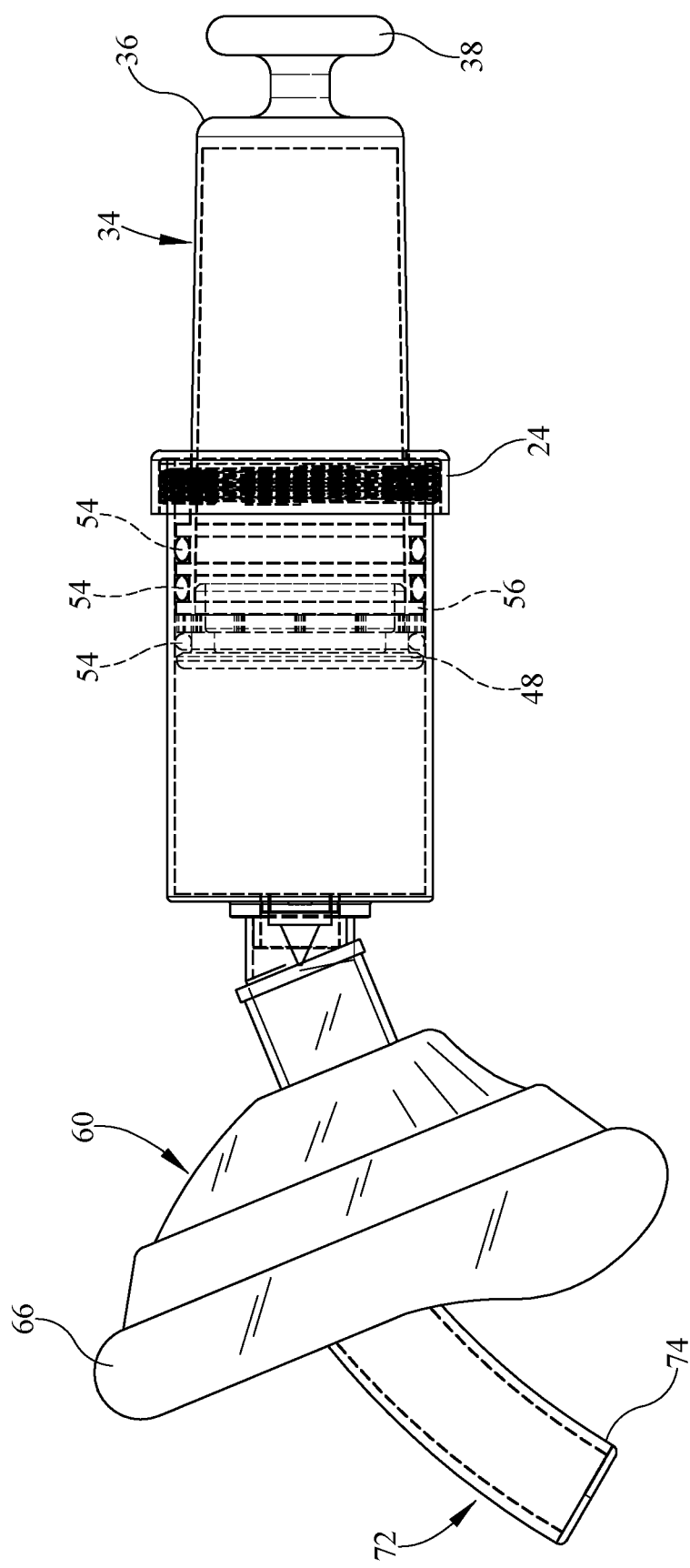
FIG. 4 is an elevation view of the airway assist device of FIG. 3 with the plunger retracted.
Figure 5:
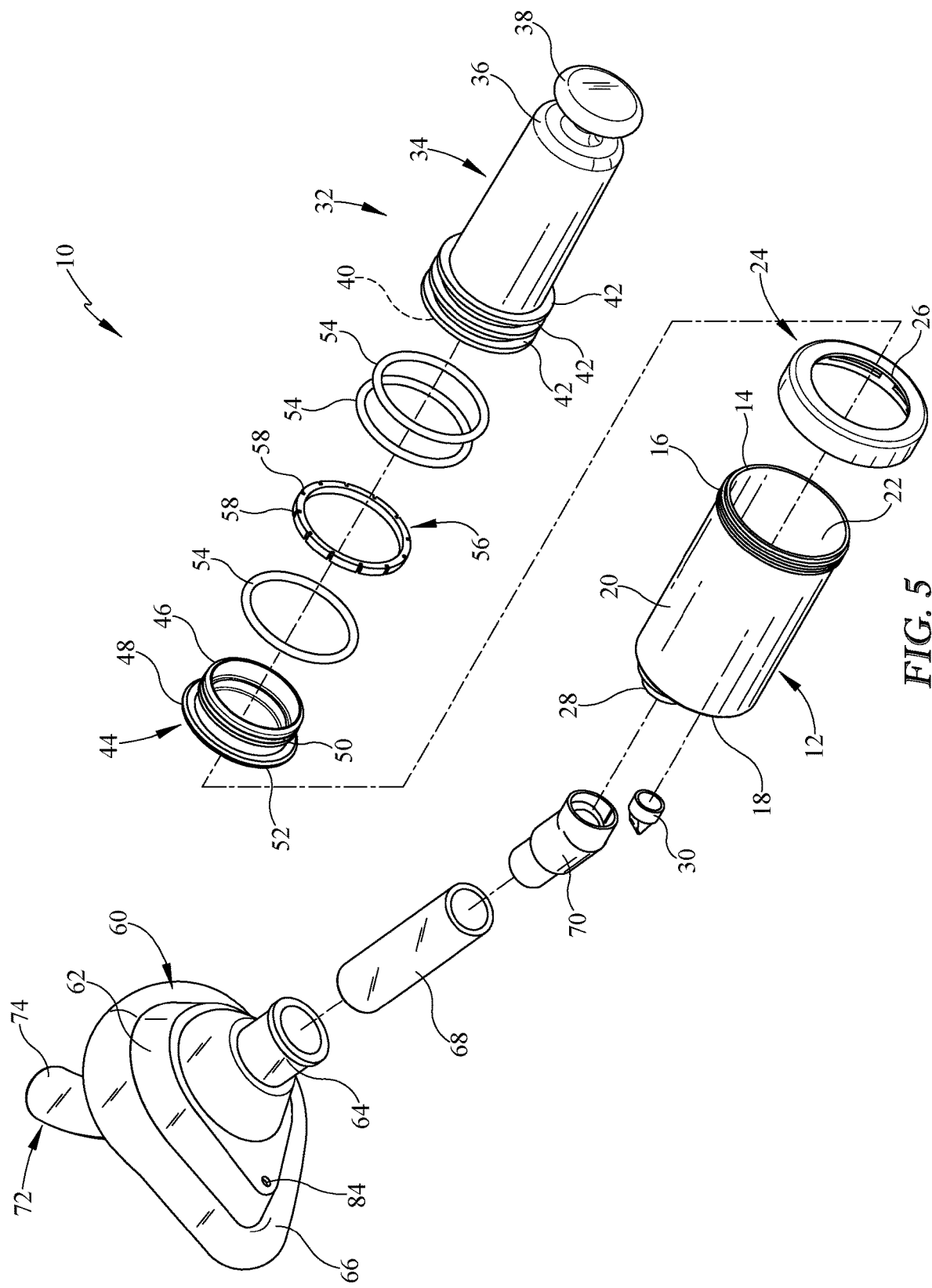
FIG. 5 is an exploded view of the airway assist device.
Figure 6:
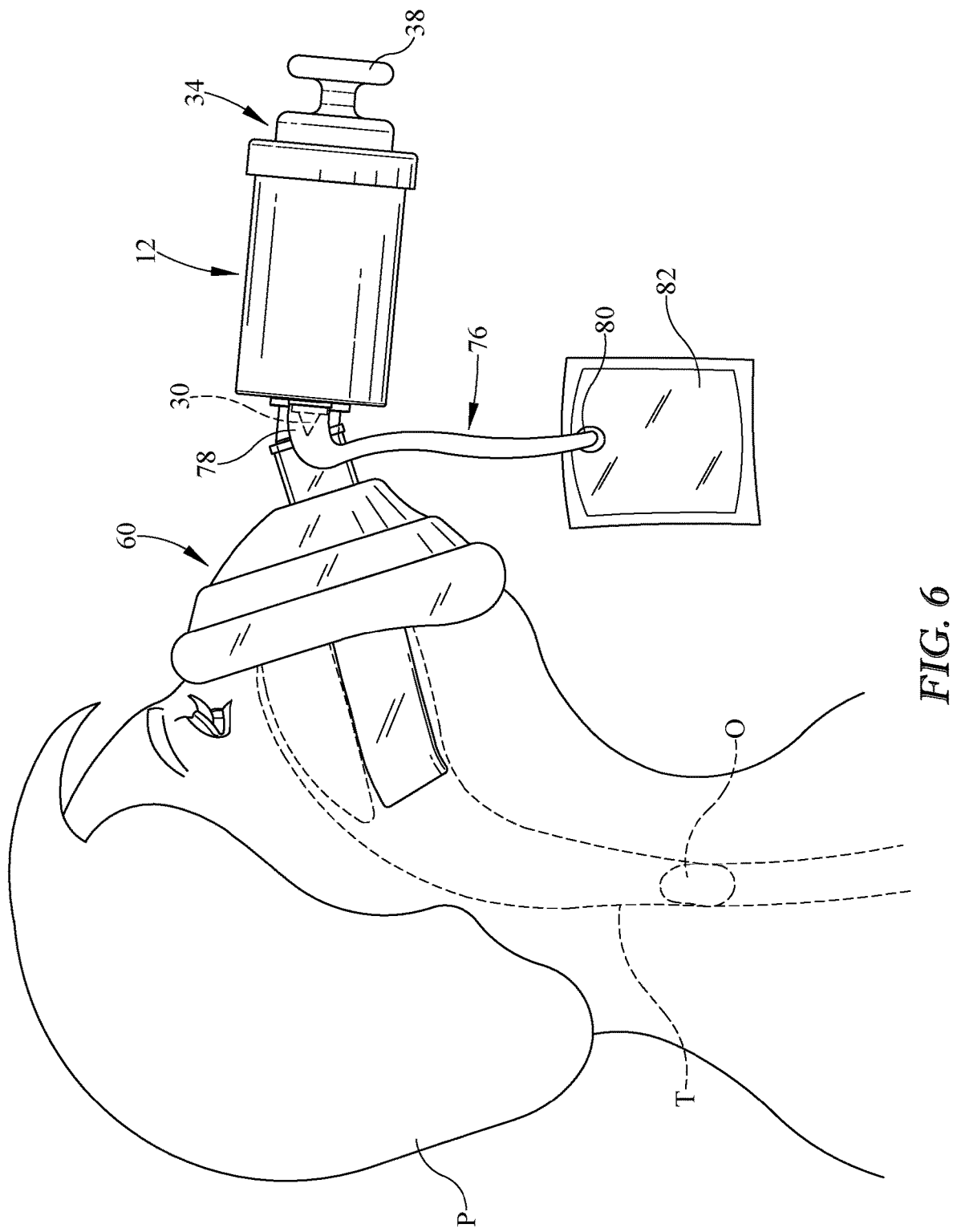
FIG. 6 is an environmental view of the airway assist device being used on a person with a fluid or other material in the throat with the optional waste receptacle attached.

Referring now to the drawings, it is seen that the airway assist device of the present invention, generally denoted by reference numeral 10, is comprised of a barrel 12 that has an open proximal end 14 having male threading 16 thereon, a distal end 18, and a medial section 20 therebetween, the barrel 12 also having a hollow interior chamber 22. A retainer ring 24 is threadably attached to the proximal end 14 of the barrel 12, the retainer ring 24 having an inwardly directed annular lip 26. An extension 28 extends outwardly from the distal end 18 of the barrel 12, the extension 28 forming an opening via its hollow passageway such that a fluid pathway exists between the interior chamber 22 of the barrel 12 and the exterior of the extension 28. The barrel 12, the retainer ring 22 and the extension 28 are each made from an appropriate plastic or similar material, preferably a bio-acceptable material and the barrel 12 and the extension 28 may be formed as single integral unit.

A positive pressure backflow valve 30 is located on the distal end 18 of the barrel 12

A plunger assembly 32 is slidably disposed within the hollow interior chamber 22 of the barrel 12 and protrudes through the proximal end 14 of the barrel 12 as well as through the retainer ring 24. As seen, the plunger assembly 32 is comprised of a plunger 34 that has a proximal end 36 with a handle 38 thereon. The plunger 34 also has a distal end 40. A series of concentric rings 42 encircle an outer surface of the plunger 34 proximate the plunger's distal end 40. The plunger 34, handle 38 and concentric rings 42 are each made from an appropriate plastic or similar material, preferably a bio-acceptable material and may be made as a single integral unit. An end cap 44 has an inner ring 46 located on a first end and an outer ring 48 located on a second end. An additional interior ring 50 is located between the inner ring 46 and the outer ring 48 and, with the inner ring 46 and outer ring 48, form a pair of channels 52 such that an O-ring 54 is received within the one of the channels 52 (the channel 52 located closer to the outer ring 48) and a relief ring 56 that has a series of longitudinal slits 58 spaced about its outer circumference, is received within the other channel 52 (the channel 52 located closer to the inner ring 46). The end cap 44 is partially inserted into the open distal end 40 of the plunger 34 and friction held therein via the inner ring 46 with the relief ring 56 abutting against the distal end 38 of the plunger 34. Additional O-rings 54 are placed into the channels formed by the concentric rings 42.

With the retainer ring 24 removed from the proximal end 14 of the barrel 12, the plunger assembly 32 is partially inserted into the interior chamber 22 of the barrel 12, distal end 40 of the plunger 34 inserted first. Once the plunger assembly 32 is so inserted, the retainer ring 24 passes over the handle 38 and proximal end 36 of the plunger 34 and is threadably attached to the proximal end 14 of the barrel 12. The plunger assembly 32 is free to slide within the interior chamber 22 of the barrel 12. When the plunger 34 is fully depressed into the interior chamber 22 of the barrel 12, the end cap 44 of the plunger assembly 32 abuts an inner surface of the distal end 16 of the barrel 12. In this position, the handle 38 and proximal end 36 of the plunger 34 protrude out of the proximal end 14 of the barrel 12. As the plunger 34 is drawn out of the proximal end 14 of the barrel 12 manually via the handle 38, the end cap 44 being solid at its base and the O-rings 48 and 54 and the relief ring 56 dimensioned to approximate the diameter of the interior chamber 22 of the barrel 12 so as to inhibit air flowing therepast, the plunger assembly 32 acts as a piston and creates a suction so as to create a vacuum within the interior chamber 22 of the barrel 12. The vacuum causes air to enter the interior chamber 22 of the barrel 12 through the open passage of the extension 28 to equalize the pressure. The slits 58 on the relief ring 56 allow just enough air therepast to act as a pressure relief opening in order to not over pressure the system. The retainer ring 24 prevents the plunger assembly 32 from being fully withdrawn from the barrel 12

A face mask 60, which may be generally tear-drop-shaped, has a dome 62, which is preferably clear. The dome 62 has a hollow stem 64 on one end. The face mask 60 has a resilient annular cuff 66, which may be self-inflating, about the dome 62. The face mask 60 is attached to the extension 28 via a hollow connector 68 that fluid flow connects the hollow stem 64 to the extension 28, either directly or via one or more other hollow connectors such as the illustrated hollow elbow connector 70. A resilient throat tube 72 has a first end (not separately numbered) that is fluid flow connected to hollow stem 64. The throat tube 72 also has a second end 74, which may be slightly curved. The hollow stem 64 and the throat tube 72 may be a single integral unit. The throat tube 72 is made from a resilient material such as pliable plastic, rubber, silicone, neoprene, etc., and is preferably a bio-acceptable grade of such material.

A flexible hose 76 has one end 78 attached to the back flow valve 30 and an opposing end 80 connected to an appropriate receptacle 82, such as the illustrated biohazard waste receptacle 82.

In order to use the airway assist device 10 of the present invention, once assembled, the plunger assembly 32 is pushed into the barrel 12 as far as possible toward the distal end 16 of the barrel 12 such that the end cap 44 essentially abuts the inner surface of the distal end 14 of the barrel 12.

The face mask 60 is attached as just described. The throat tube 72 is attached to the hollow connector 66 as described if they are not a single unit. The flexible hose 76 and its waste receptacle 72 are each attached as described. The opposing end of the throat tube 72 is pushed into the throat T of the person P having a fluid or other material O within his or her throat T. The curved and resilient nature of the throat tube 72 allows the throat tube 72 to curve with the curvature of the person's mouth and throat T. As the throat tube 72 is inserted into the person throat T, the face mask 60 becomes positioned over the person's face F with the cuff 66 providing a seal about the person's mouth and nose. The throat tube 72 is dimensioned such that once the face mask 72 is properly fitted on the person's face F, the throat tube 72 is at a proper intubation depth so that the face mask 60 also acts as a stop and helps prevent over insertion of the throat tube 72 into the throat T which can cause the fluid or other material O in the person's throat T to be pushed deeper.

When the airway assist device 10 is properly positioned within the person's throat T, the plunger assembly 32, being fully depressed, is drawn outwardly via the handle 38 such that the plunger assembly 32 creates a suction within the barrel 12 and within the throat tube 72 which causes air to be drawn into the throat tube 72 from the second end 76 thereof, which air is drawn upward through the throat T. This drawn air creates suction within the throat T which suction helps draw the fluid or other material O up and out of the throat T. A small opening 84 on the face mask 60 helps prevent over pressurization at the face mask 60. When the plunger assembly 32 is fully extended, the retainer ring 22 prevents the plunger assembly 32 from being removed from within the barrel 12.

The clear nature of the dome 62 of the face mask 60 allows a user to be able to see what is occurring about the person on which the device 10 is being used, such as, for example, if the person has vomited, so that appropriate action can be taken. If the person has vomited or the fluid extracted is within the interior chamber 22 of the barrel, then the mask 60 is quickly removed from the person, the throat tube 72 is manually closed off in appropriate fashion (pinching the throat tube 72, covering the open second end 74 with a hand or other object, etc.) and the plunger assembly 32 is pushed into the barrel 12 so as to create positive pressure therein. This positive pressure opens the backflow valve 30 and allows the vomit or other fluid to exit through the backflow valve 30 where the vomit passes through the flexible hose 76 and is captured in the receptacle 82 for eventual appropriate disposal. Once the barrel 12 and any of the connecting tubes are clear of the vomit or other fluid, the throat fluid or other material clearing procedure is once again resumed as needed.

For a particularly deep lodged fluid or other material O, a second iteration of use of the device 10 may be needed by lifting the face mask 60 from the person's face to unseal therefrom and so as to remove the throat tube 72 from the person's throat T, depressing the plunger assembly 32 back into the barrel 12, and reiterating the steps just described.

The airway assist device 10 may come in various sizes for various sized people P such as a child sized airway assist device 10 and an adult sized airway assist device 10 with the size and length of the throat tube 72 and the size of the face mask 60 being adjusted accordingly (of course, more than two sizes are possible).

As an additional option, an electronic sound producing device (not illustrated) can be located on an appropriate location of the airway assist device 10, which sound producing device has a prerecorded message thereon (on a memory chip) such that the pressing of a button triggers activation of the sound producing device which produces the message through a speaker (piezo-electric speaker, or similar), which message is instructions on proper use of the airway assist device 10 so that a person not familiar with the airway assist device 10 presses the activation button and listens to the instruction on proper device 10 usage, which instructions can be paused or replayed s needed. Of course a small written message is placed on the airway assist device 10 instructing a user to depress the activation button in order to receive the instructional message. Visual instructions can be imprinted on the side of the barrel 12

While the invention has been particularly shown and described with reference to an embodiment thereof, it will be appreciated by those skilled in the art that various changes in form and detail may be made without departing from the spirit and scope of the invention.

I claim:

1. A suction device, comprising:
   a barrel having an open barrel proximal end and a barrel distal end having an opening;
   a plunger slidably disposed within said barrel, said plunger having a plunger proximal end and a plunger distal end;
   a plunger cap having a solid flat base disposed on said plunger distal end,
      wherein said plunger protrudes through said barrel proximal end with said solid flat base of said plunger cap engaged to an inner surface of said barrel distal end;
   a handle attached to said plunger proximal end of the plunger;
   a face mask having a dome extending to a dome outer periphery engaged to an annular cuff;
   a resilient tube having a tube first end fluidically connected to said opening on said barrel distal end and a tube second end, said resilient tube passing through the dome of the face mask;
   an outer ring and an inner ring disposed in a spaced apart relation about said plunger cap;
   a first O-ring encircling said plunger cap and disposed between said outer ring and said inner ring of said plunger cap;
   a first concentric ring encircling said plunger proximate said plunger distal end; and
   a relief ring disposed between said first O-ring and said first concentric ring, said relief ring concentric with said first O-ring;
   wherein outward draw of said plunger creates suction drawing air into said barrel through said opening on said barrel distal end, causing air to be drawn into said tube second end.

2. The suction device as in claim 1, wherein the relief ring has at least one longitudinal slit in a relief ring outer surface, said at least one longitudinal slit open to opposite relief ring faces to allow air to pass therethrough, thereby regulating a pressure of said suction within said barrel upon sliding said plunger within said barrel.

3. The suction device as in claim 2, further comprising a second concentric ring encircling said plunger and a second O-ring disposed between said first concentric ring and said second concentric ring.

4. The suction device as in claim 3, further comprising a third concentric ring encircling said plunger and a third O-ring disposed between said second concentric ring and said third concentric ring.

5. The suction device as in claim 2, wherein said relief ring has a plurality of longitudinal slits disposed in a spaced apart relation about said relief ring outer surface.

6. The suction device as in claim 1, further comprising a positive pressure backflow valve disposed on said barrel distal end.

7. The suction device as in claim 6, further comprising a receptacle connected to said backflow valve.

8. The suction device as in claim 1, further comprising a sound producing device attached to said barrel or to said plunger or to said face mask.

9. The suction device as in claim 1, further comprising a retainer cap having an inwardly directed annular lip, said retainer cap removably attached to said barrel proximal end, an additional concentric ring engageable with said annular lip to prevent withdrawal of said plunger from said barrel.

10. The suction device as in claim 1, wherein said annular cuff comprises a self-inflating annular cuff.

11. The suction device as in claim 1, wherein said resilient tube comprises a pliant tube selected from the group consisting of rubber, silicone and neoprene.

12. The suction device as in claim 1, wherein said dome comprises a clear material allowing a user to observe a subject configured to be engaged to said face mask and a material (O) drawn up from a throat (T) of the subject.

13. A suction device, comprising:
a barrel having an open barrel proximal end and a barrel distal end having an opening;
a plunger slidably disposed within said barrel, said plunger having a plunger proximal end and a plunger distal end;
a plunger cap having a solid flat base disposed on said plunger distal end,
wherein said plunger protrudes through said barrel proximal end with said solid flat base of said plunger cap engaged to an inner surface of said barrel distal end;
a handle attached to said plunger proximal end of the plunger;
a face mask having a dome extending to a dome outer periphery engaged to an annular cuff;
a resilient tube having a tube first end fluidically connected to said opening on said barrel distal end and a tube second end, said resilient tube passing through the dome of the face mask;
a positive pressure backflow valve disposed on said barrel distal end; and
a material collection receptacle connected to said positive pressure backflow valve;
wherein outward draw of said plunger creates suction drawing air into said barrel through said opening on said barrel distal end, causing air to be drawn into said tube second end.

14. The suction device as in claim 13, further comprising:
an outer ring and an inner ring disposed in a spaced apart relation about said plunger cap;
a first O-ring encircling said plunger cap and disposed between said outer ring and said inner ring of said plunger cap;
a first concentric ring encircling said plunger proximate said plunger distal end; and
a relief ring disposed between said first O-ring and said first concentric ring, said relief ring concentric with said first O-ring.

15. The suction device as in claim 14, wherein the relief ring has at least one longitudinal slit in a relief ring outer surface, said at least one longitudinal slit open to opposite relief ring faces to allow air to pass therethrough, thereby regulating a pressure of said suction within said barrel upon sliding said plunger within said barrel.

16. The suction device as in claim 15, further comprising a second concentric ring encircling said plunger and a second O-ring disposed between said first concentric ring and said second concentric ring.

17. The suction device as in claim 16, further comprising a third concentric ring encircling said plunger and a third O-ring disposed between said second concentric ring and said third concentric ring.

18. The suction device as in claim 15, wherein said relief ring has a plurality of longitudinal slits disposed in a spaced apart relation about said relief ring outer surface.

19. The suction device as in claim 13, further comprising a sound producing device attached to said barrel or to said plunger or to said face mask.

20. The suction device as in claim 13, further comprising a retainer cap having an inwardly directed annular lip, said retainer cap removably attached to said barrel proximal end, an additional concentric ring engageable with said annular lip to prevent withdrawal of said plunger from said barrel.

21. The suction device as in claim 13, wherein said annular cuff comprises a self-inflating annular cuff.

22. The suction device as in claim 13, wherein said resilient tube comprises a pliant tube selected from the group consisting of rubber, silicone and neoprene.

23. The suction device as in claim 13, wherein said dome comprises a clear material allowing a user to observe a subject configured to be engaged to said face mask and a material (O) drawn up from a throat (T) of the subject.

* * * * *